(12) United States Patent
Segev (10) Patent No.: US 8,482,743 B2
(45) Date of Patent: Jul. 9, 2013

(54) METHOD AND SYSTEM FOR OPTICAL EDGE MEASUREMENT

(75) Inventor: Avner Segev, Tel Mond (IL)

(73) Assignee: Cognitens Ltd., Ramat Hasharon (IL)

( * ) Notice: Subject to any disclaimer, the term of this patent is extended or adjusted under 35 U.S.C. 154(b) by 1535 days.

(21) Appl. No.: 11/665,978

(22) PCT Filed: Jun. 20, 2005

(86) PCT No.: PCT/IL2005/000660
§ 371 (c)(1),
(2), (4) Date: Apr. 23, 2007

(87) PCT Pub. No.: WO2006/048857
PCT Pub. Date: May 11, 2006

(65) Prior Publication Data
US 2007/0297665 A1 Dec. 27, 2007

Related U.S. Application Data

(60) Provisional application No. 60/623,769, filed on Nov. 1, 2004.

(51) Int. Cl.
*G01B 11/14* (2006.01)
(52) U.S. Cl.
USPC .......................................................... 356/625
(58) Field of Classification Search
USPC .................................................. 356/600–645
See application file for complete search history.

(56) References Cited

U.S. PATENT DOCUMENTS

| | | | |
|---|---|---|---|
| 2,397,702 A | 4/1946 | Smith et al. | |
| 2,432,928 A | 12/1947 | Palmquist | |
| 2,440,584 A | 4/1948 | Heltzer et al. | |
| 2,543,800 A | 3/1951 | Palmquist et al. | |
| 4,104,102 A | 8/1978 | Eagon et al. | |
| 4,680,704 A * | 7/1987 | Konicek et al. | 382/100 |
| 4,873,651 A * | 10/1989 | Raviv | 700/259 |
| 5,619,587 A | 4/1997 | Willoughby, Jr. et al. | |
| 6,028,672 A | 2/2000 | Geng | |
| 6,125,197 A | 9/2000 | Mack et al. | |
| 6,546,356 B1 | 4/2003 | Genest | |
| 7,623,250 B2 * | 11/2009 | Moctezuma de la Barrera et al. | 356/604 |
| 2004/0114153 A1 | 6/2004 | Andersen et al. | |

FOREIGN PATENT DOCUMENTS

| | | |
|---|---|---|
| DE | 38 05 455 A1 | 8/1989 |
| DE | 102 54 542 A1 | 1/2004 |

(Continued)

OTHER PUBLICATIONS

Ziou, D., et al., "Edge Detection Techniques—An Overview", *Journal of Pattern Recognition and Image Analysis*, vol. 8, No. 4, pp. 537-559, (1998).
Hastedt, H., et al., "Image-Variant Interior Orientation and Sensor Modelling of High-Quality Digital Cameras", ISPRS Symposium Comm. V, Korfu, 2002.

*Primary Examiner* — Tara S Pajoohi Gomez
(74) *Attorney, Agent, or Firm* — Vorys, Sater, Seymour and Pease LLP; Susanne M. Hopkins; William L. Klima (57) ABSTRACT

Edge data for an object are obtained by placing the object in front of a medium that has greater reflectance than the object, and both are illuminated by a light source. The contrast in image intensity obtained between the object and background enables the edges of the object to be determined.

22 Claims, 5 Drawing Sheets

FOREIGN PATENT DOCUMENTS

| | | |
|---|---|---|
| EP | 0 113 691 A2 | 7/1984 |
| EP | 0 962 745 A1 | 12/1999 |
| WO | 02/19687 A2 | 3/2002 |
| WO | 2005/010825 A2 | 2/2005 |

* cited by examiner

METHOD AND SYSTEM FOR OPTICAL EDGE MEASUREMENT

CROSS-REFERENCE

This is a National Phase Application filed under 35 U.S.C. 371 of International Application No. PCT/IL2005/000660, filed Jun. 20, 2005, claiming the benefit under 35 USC 119(e) of U.S. Provisional Application No. 60/623,769, filed Nov. 1, 2004, the entire contents of each of which is hereby incorporated herein by reference in its entirety.

FIELD OF THE INVENTION

This invention relates to optically-based methods and systems for dimensional measurement of objects. In particular, the invention is directed to measurements relating to free edges of such objects, especially where the objects are highly reflective and/or textured.

BACKGROUND OF THE INVENTION

Optical measurements of the edges of manufactured objects are of great value in industry, but in practice such measurements are often difficult to accomplish with great accuracy or confidence. Industrially manufactured objects such as automotive metal parts, plastic parts and so on typically vary in their optical reflectance properties, some being more reflective than others for a given incident beam intensity. Furthermore, similar parts that are manufactured from the same specifications, for example a series of car door panels of the same model, also vary from one another in terms of the local reflectance properties that these parts exhibit near the edges of the parts. These variations are usually attributable to the manufacturing process and variations in the raw material properties between the parts. There are often part to part and batch to batch manufacturing variations due to progressive wear and tear of the manufacturing tools, differences between several production lines that manufacture the same parts, and so on. For example, the sheet metal used for the manufacture of many automotive parts is comprised of carbon and ferrite: small differences in the ratio of carbon to ferrite, and/or in the thickness of the sheet metal, coupled with different coatings and treatments that may be applied can lead to relatively large variations in the optical reflectance characteristics of the manufactured parts. Further, when attempting to generate an image of an edge-comprising part, the edge reflectance characteristics of the part, which may include for example specular reflections, surface texture and other forms of optical interferences near the edge, can cause the edge or part thereof in the image to appear shifted relative to where the true mechanical edge of the part should appear in the image.

Machine vision systems often utilize different illumination schemes to overcome such problems. For example, use of polarized illumination helps to reduce specular reflections that often result in image saturation, reducing the image saturation and thus providing a more accurate image of the edges. Alternatively, the image acquisition system may be provided with filters of different spectral bands to filter out of the image texture that interferes with the edge measurement. Back illumination methods are based on illuminating the object from behind, and this has the result of inverting the polarities in the image, i.e. the object appears as dark and the background as bright in the image. While effective to varying degrees, these methods nevertheless add significant complexity to the image acquisition systems. Moreover, it is not possible in all applications to apply such techniques, for example when the objects being imaged are large objects such as for example some automotive parts, which would require large and complex back illumination systems.

SUMMARY OF THE INVENTION

Herein, the term "correspondence" refers to point to point mapping between different images of an object, typically at the pixel level, for example based on neighborhood-type coding.

The term "labeling" is used herein to refer to the proper identification of patterns such as one-dimensional line patterns or quasi one dimensional stripe patterns between different images of an object.

The term "matching" refers to sub-pixel to sub-pixel mapping between different images of an object.

The term "image", in addition to the regular usage, is also used herein -to include an original pattern that is projected onto an object.

The term "gain" herein includes the ratio of the reflectance of a surface of an object to the reflectance obtained from a standard white diffuser surface under the same illuminating conditions, and the ratio is often expressed in log scale.

The term "reflectance" refers to the ratio of radiant flux (total power emitted, received or passing in the form of electromagnetic radiation) reflected by a surface to the radiant flux falling on it. However, reflectance is often expressed as a percentage, i.e., the radiant flux reflected by a surface as a percentage of the radiant flux falling on it.

In the present invention, a methodology is provided for reconstructing 3D surface structure of an object. The term "object" includes any two or three dimensional object or a collection of objects including a scene.

According to the present invention, preferably a retro reflective material or other suitably reflective material is placed behind the object to be measured as an optical background. A suitable front illumination system, typically adjacent to the camera(s) is used to illuminate the object and the reflective background. The reflection gain of the reflective material is preferably high, so that low illumination powers are required to achieve high signals in the image. The signal reflected off of the object is small because of the low illumination powers together with the mostly diffuse reflection properties, i.e., low gain, of the object. Overall the resultant image is bright in the areas thereof corresponding to the background and dark in the areas corresponding to the object. With this method, the problems posed by the reflection properties of the object near the edge do not come in to play in the resultant image, and the true edge can be found with relative ease.

Thus, according to the invention, a method is provided for providing edge data useful in procedures associated with the dimensional measurement of an object, comprising:

(a) obtaining at least one image of a desired edge of a surface of an object contrasted with a background medium, wherein the surface and medium are front-illuminated, and wherein the medium comprises a reflectance substantially greater than a reflectance of said surface at least in a vicinity of said edge at least when viewed along an image viewing axis associated with said at least one image; and (b) analysing said image to obtain edge data from an interface between adjacent areas of different optical contrast therein corresponding to one or the other of said surface and said medium.

Step (a) comprises:

aligning said surface and said edge with respect to an image viewing axis of at least one image capturing device, such that said surface and edge are positioned intermediate between said at least one image capturing device and said background medium;

front illuminating at least a portion of said surface including said edge and at least a portion of said medium proximate to said edge;

obtaining at least one image of at least said portion of said surface comprising said edge and including said portion of said medium as viewed from said viewing axis of said at least one image capturing device.

Typically, in step (a), said at least one image comprises at least one first image area corresponding to said portion of said surface comprising said at least one edge and at least one second image area corresponding to a portion of said medium proximate to said at least one edge, wherein an interface between the or each said first image area and the or each said second image area corresponds to said at least one edge; and step (b) comprises determining the coordinates on said image corresponding to the interface.

The medium preferably has a gain greater than about unity, and more preferably greater than about 2, and the medium optionally comprises a retro-reflective layer.

The aforementioned procedures may include, for example, a procedure for comparing a profile of said edge as viewed along a particular viewing axis with a datum profile.

Optionally, the method further comprises the step of determining geometrical parameters of said edge from said comparison. These geometrical parameters may include, for example, any one of: a center of curvature of the edge; a characteristic dimension of the edge; departure of the edge from a nominal profile. The characteristic dimension may include, for example, any one of a radius of curvature or diameter when relating to an internal circular edge, for example, or to an external circular or cylindrical edge, or indeed to a characteristic width, and so on.

Alternatively, the procedures may include a procedure for determining the three dimensional profile of said edge. In such a case, step (a) may comprise obtaining a set of first images comprising at least two first images of said edge along different viewing axes; the method further comprising the step of matching corresponding points of the edge between the at least two first images to obtain a series of matched points, and the step of determining the 3D profile of said edge from said series of matched points. The step of matching corresponding points between images may comprise: illuminating said surface with a structured pattern and obtaining a set of second images of the thus illuminated object along said different viewing axes corresponding to said set of first images; for each said second image superimposing a corresponding first image, at least in a virtual sense, finding intersections between said pattern therein and a said interface of the corresponding said first image to provide a series of intersection points for said second image; matching elements corresponding to intersection points of one second image with the intersection points of another said second image; determining 3D coordinates from said matched elements. Typically, the 3D coordinates are determined using a suitable triangulation or epipole method applied to said matched elements, or any other suitable method.

The method of the invention may be applied to any suitable object having internal or external edges, for example a mechanical component, such as automotive component, for example.

The present invention also relates to a system for providing edge data useful in procedures associated with the optical measurement of surfaces of an object having at least one edge, comprising:

at least one image capturing device for capturing at least one image of at least said edge from a viewing axis;

a background medium, wherein the medium comprises a reflectance substantially greater than a reflectance of said surface of the object at least in a vicinity of said edge;

the at least one image capturing device being disposed with respect to said medium such that said surface and edge are positioned intermediate between said at least one image capturing device and said medium;

illumination means for front illuminating at least a portion of said surface including said edge and at least a portion of said medium proximate to said edge;

microprocessor means for analysing image captured by said at least one image capturing device to obtain edge data from an interface between adjacent areas of different optical contrast therein corresponding to one or the other of said surface and said medium.

In one embodiment, two or more said image capturing devices may -be provided, each said image capturing device positioned at a different relative viewing axis with respect to said object.

In such or other embodiments, two or more said optical reflective mediums may be provided, wherein each said medium is positioned such that the object is aligned between a said medium and at least one said image capturing device.

The medium may be made from a material having suitable reflectance properties, and/or comprise a coating having suitable reflectance properties, and/or comprise an outer layer configured such as to exhibit (and/or made from a material having) suitable reflectance properties.

Typically, the medium comprises a retro-reflective layer and in any case the medium typically comprises a gain of greater than unity, or preferably of about 2 or greater than 2.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 9b is an image of the object and background medium of FIG. 9a.

DETAILED DESCRIPTION OF THE INVENTION

Figure 1:
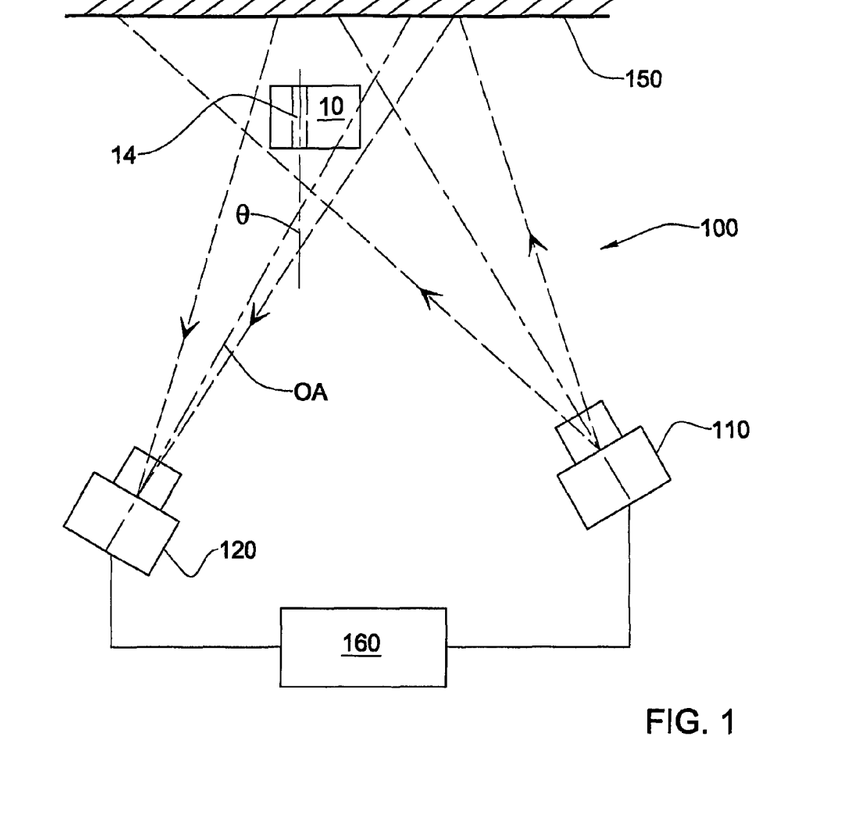
FIG. 1 is a schematic illustration of the elements of a first embodiment of the system of the invention.

A system according to a first embodiment of the invention is illustrated in FIG. 1. The system, generally designated with the numeral 100, comprises at least one illumination source 110, a light reflecting medium 150, and at least one optical image capturing device 120.

An object 10 to be imaged, typically comprising surfaces and edges 12 of interest, is placed in front of the medium 150, and arranged such that it is located between the medium 150 and the illumination source 110, and also between medium 150 and the image capturing device 120. In particular, the illumination source 110 is spatially arranged with respect to the object 10 and medium 150, such that, at least during operation of the system 100, the object 10, or at least a portion of the surface thereof comprising edges 12, and a part 152 of the medium 150 surrounding the edges 12 are illuminated by the source 110. While edges 12 are external edges of the object 10, the present invention also relates to internal edges, for example edge 13 of a bore hole 14 through the object, wherein a corresponding part 15 of the medium 150 may be seen via the hole 14. Thus, while the description herein will refer generally to external edges, it is to be understood that the invention similarly applies to internal edges where appropriate, mutatis mutandis.

Thus, the object 10 can comprise any mechanical or physical object that it is desired to determine edges thereof. The object 10 may comprise surfaces and edges 12 that may be substantially three-dimensional, for example fabricated automotive parts such as die-pressed door or body panels. Alternatively the object 10 may comprise surfaces and edges 12 that may be considered "two-dimensional", comprising, for example, a thin metal sheet having a particular plan form—useful in quality control of the shape of formers before being pressed in dies or the like.

Figure 2:
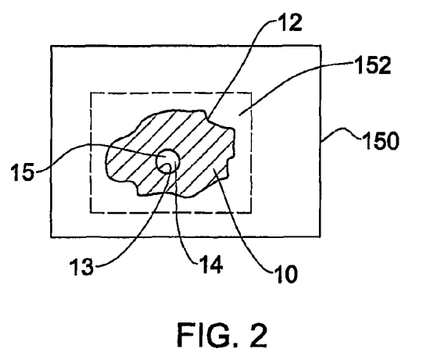
FIG. 2 is a view of the object and background medium of the system of FIG. 1 as viewed along the optical axis of the image capturing device thereof.

Similarly, the image capturing device 120 is spatially arranged with respect to the object 10 and medium 150, such that, at least during operation of the system 100, an image of the object 10, or at least a portion of the surface thereof comprising edges 12, and a part of the medium 150 surrounding or proximate to the edges 12, may be obtained with the image capturing device 120 (FIG. 2).

In operation, the illumination source 110 illuminates the object 10 and medium 150, or at least a portion of the surface of the object 10 including edges 12 of interest, and a part 152 of the medium 150 surrounding the edges 12, as seen by the image capturing device 120, and the image capturing device 120 then captures one or more images of the scene including edges 12 and portion 152.

The said image capturing device 120 may comprise any suitable image capturing device or system, typically a suitable camera, for example a video camera or any CCD-or CMOS-based camera, which can transmit an image electronically to a microprocessor means 160 such as a suitable computer via an image grabber, for example. The microprocessor means 160 may also be optionally configured to control the illumination source 110, typically to synchronize illumination of the object with the image taking process by means of the devices 120.

The illumination source 110 may comprise any suitable illumination means, typically a suitable projector or light emitter, further typically illuminating in white light, but optionally capable of illuminating the object in any other wavelength in the visible spectrum, or indeed outside of the visible spectrum including infra red and ultraviolet wavelengths, for example. The illumination source 110 may comprise for example suitable discharge lamps, LED's, lasers and so on.

The light reflecting medium 150 is characterized in having a high reflectivity or gain, particularly relative to the reflectivity or gain of the object 10, in particular the part of the surface thereof including the edges 12.

The medium 150 typically comprises a retro-reflective layer having a retro-reflective surface, however, many other reflective, semi reflective or even matte surfaces may be suitable, for example matte white. As will become clearer herein, the minimum gain or reflectance provided by the medium 150 is typically related to the gain or-reflectance properties of the object 10 itself. Thus, the more reflective the object 10 itself is, the higher the reflectivity or gain of the medium 150 needs to be in order to provide adequate contrast when viewed by the image capturing device 120. Thus, the gain or reflectance of the object 10, in particularly the edges or the zones or areas of the object 10 containing the edges 12, is substantially lower than the gain or reflectance of the medium 150. For example, the object 10 may have a gain of less than unity and/or reflectance less than about 5%, while the medium 150 may have a gain of unity or greater, including 2, 3, 4, and so on, and/or reflectance of more than 5%, say 10%, 15%, 20%, 30%, 40% and so on. Alternatively, the object may have a gain of 1 or greater than 1, e.g., 1.3, and/or a reflectivity of greater than 5%, say 10%, wherein the medium 150 is chosen having a gain of substantially more than 1.3, say 2 or greater than 2, and/or a reflectivity of substantially more than 10%, say 20% or greater.

In other words, the ratio of the medium gain $G_M$ to the object gain $G_O$ is greater than 1, i.e., the ratio of medium reflectance $R_M$ to object reflectance $R_O$ is greater than 1. Said differently, for a given radiant flux falling on the medium 150 and object 10, the ratio of radiant flux emitted by the medium 150 to the radiant flux emitted by the object 10 (herein referred to as the "radiant flux ratio"), in particular the surface thereof close to edge 12, is greater than 1.

A "retro-reflective surface" is a surface which bounces incident light back towards the source of the light, in other words, a light beam that has a certain incidence angle with respect to the layer will exit the layer at approximately the same angle back to the illumination source. Such retro-reflective surfaces are well known and may be formed, for example, using spherical reflective beads, or the like, and compositions of retro-reflective layers and methods for their production are disclosed in U.S. Pat. Nos. 2,432,928, 2,440,584, 2,543,800, 2,397,702, 4,104,102, for example, the contents of which are incorporated herein in their entirety by reference. Retro-reflective surfaces typically provide a gain of more than 2.

In the embodiments disclosed herein, the illumination source 110 is located relatively close to the one or more image capturing devices 120, and thus illumination light from the illumination source 110 is captured at relatively high intensity by the image capturing devices 120 after being reflected by the medium 150.

In other embodiments, where the illumination source(s) 110 and the image capturing device(s) are located at significantly spaced spatial positions, such that a retro reflective surface would not reflect most of the light incident on it to the image capturing device(s), then the medium 150 comprises a reflective surface that is configured for reflecting a significant portion of the incident light thereon towards the image capturing device(s). For example, the background medium 150 may be oriented with respect to the viewing axis of the image capturing devices 120 such as to provide such an effect. In cases where there are a plurality of image capturing devices 120, all of which are located in significantly different positions relative to the source 110, the medium is adapted for reflecting the incident light in all the required viewing directions, each defined by the viewing axis of a corresponding image capturing device 120, so that the medium 150 is perceived by each device 120 as being highly reflective.

Thus, and particular for such cases, the medium 150 may comprise any suitable reflective, semi reflective or even matte surfaces, typically depending on the reflectance of the object 10 itself, particularly capable of reflecting the incident light in the required directions with high gain. Non-limiting examples of suitable materials for the medium 150 may include the Matte White, High Contrast Matte White, Video Spectra, Glass Beaded, Silver Matte, High Power, and Silver Vision screen fabrics manufactured by Da-Lite (USA); Mocom 20X screens provided by Mocomtech; and so on.

The medium 150 is typically a rigid planar screen having a suitable retro-reflective, reflective, semi reflective or matte surface on a suitable substrate, for example glass or plastic. Alternatively, the medium may be non-planar, and comprise, for example, a concave form. Alternatively, the medium 150 may be flexible and roll-up, and held in place in extended mode behind the object 10 by means of a stand or frame when the system 100 is in operation.

Figure 3:
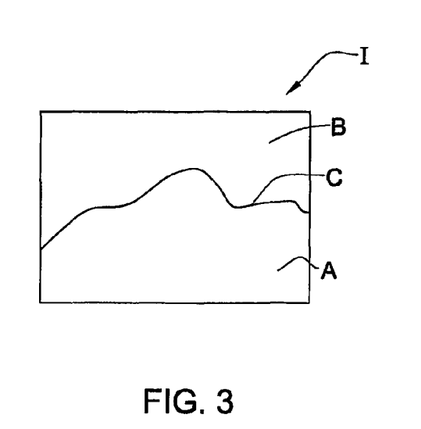
FIG. 3 is an image of the object and background medium of the system of FIG. 1 taken by the image capturing device thereof.

FIG. 3 illustrates a typical image I obtained by one image capturing device 120 using the system 100. The image I comprises a relatively dark zone A corresponding to the surface of the object 10 as viewed by the image capturing device 120 along its viewing axis OA, which sharply contrasts with a relatively bright zone B adjacent to and typically surrounding at least a part of zone A and corresponding to part 152 of the medium 150, which reflects light from the source 110 directly to the image capturing device 120 with high reflectivity. The contrast between areas A and B are due to the difference in the reflectance or gain between the object 10 and the medium 150.

The one or more images obtained by the image capturing device 120, for example image I, are transmitted to a suitable microprocessor 160 which analyses the images. Generally, the first step in such analyses is to identify the two dimensional (2D) interface or edge C between the dark zone A and the bright zone B on the image I itself, and this interface or edge C should correspond to the mechanical edge 12 when the object 10 is viewed along the optical axis OA (also referred top herein as "image viewing axis" or "viewing axis") of image capturing device 120. This step typically involves dividing the image I into pixels, and determining a set of pairs of pixels wherein, for each said pair of pixels, which are adjacent pixels in the image I, one pixel has a light intensity which is significantly higher than the light intensity of the other pixel. Alternatively, any suitable edge detection method, including sub-pixel edge detection methods, can be used for determining edge C, for example as disclosed in "*Edge Detection Techniques—An Overview*", D. Ziou and S. Tabbone, International Journal of Pattern Recognition and Image Analysis, Vol. 8, No. 4, pp. 537-559, 1998.

The next step in such analysis can take any one of various forms, depending on the specific application of the method of the invention. For example, it may be desired to check predetermined profiles of 3D mechanical components when viewed from certain directions, which appear as 2D profiles, or indeed of 2D edges of a sheet member, for example, against nominal profiles, which may be stored in processor 160. Such analysis may be useful in some forms of quality control. For example, in the mass manufacture of a certain mechanical component, it may be necessary for a part thereof, for example a tab or bracket, to have dimensions within tight tolerances. In mechanical parts, discrete edge points of interest, for example of the aforesaid tab or bracket, must be measured accurately, as at these points the part is assembled to other parts to form an assembly. Particularly if these tabs or brackets are on the outside of the component and comprise edges the profile of which is indicative of the manufacturing tolerance, these edges may be accurately imaged using the system of the invention. The profile of the edges can be compared with nominal profiles stored in the processor 160, for example, using any suitable software.

Similarly, through holes or slots are also important for the same reason and may be measured by determining their accurate edge positions. Indeed the critical dimensions of interest to the user of the present invention may refer to internal edges of through-holes or the like, wherein the medium 150 can be viewed through the said holes along the viewing axis of the image capturing devices 120.

In some specific cases, not necessarily restricted to this embodiment, it may be advantageous to mount a background medium to the object, or to mount a plurality of background media to various parts of the object, near to the edges of interest. For example different parts of the object may comprise drastically different reflectivities, and it may be desired in some cases to provide different background media to each part of the object, each background medium having a reflectivity higher than that of the corresponding part of the object by a given ratio, for example, rather than using a single background medium that may be very reflective with respect to one part of the object, while marginally reflective with respect to a very reflective pat of the object. Alternatively, this may be of particular interest in the case of, for example, a container having a bore to an inside chamber thereof, but the bore not being visible from the opposite side of the container. Thus, placing a background medium behind the container would not enable the same to be viewed via the bore. Accordingly, in such cases, a suitably sized piece of background medium is mounted inside the container behind the bore, preferably aligned orthogonally to the axis of the bore, and this background piece may thereby be illuminated via the bore, and thus the edges of the bore measured according to the invention.

In any case, the profile of the edge of a particular bore or slot, obtained according to the invention, can be compared with a datum profile in any number of ways, and dimensional data obtained therefrom. For example, when applying the invention to a circular bore in a machine component, if the viewing axis OA is at an angle $\theta$ to the axis of the bore, then the edge of the bore should appear in the image I as an ellipse. The aspect ratio of the ellipse (i.e., ratio of the major axis to the minor axis) is determined by the magnitude of this angle $\theta$. The microprocessor 160, having been input the angle between the viewing axis OA and a particular datum of the object, determines the edge of the bore, and compares the profile with a best-fit ellipse according to predetermined criteria. Such a datum may comprise a particular reference point or set of points with respect to which all other dimensions of the object are referenced. If the aspect ratio of the fitted ellipse is different from that expected at angle $\theta$, then it may be suspected that either the bore is misaligned with respect to the aforesaid datum (and therefore with the viewing axis OA), and/or that the surface of the object in the immediate vicinity of the bore (and thus the edge of the bore) may be on a plane that is tilted with respect to the axis of the bore. Further analysis of the profile of the edge relative to the fitted ellipse may yield the coordinates of the center of the bore, for example, and/or deviations of the measured edge profile from the best-fit ellipse perimeter may provide an indication of the roundness of the bore itself.

Figure 9A:
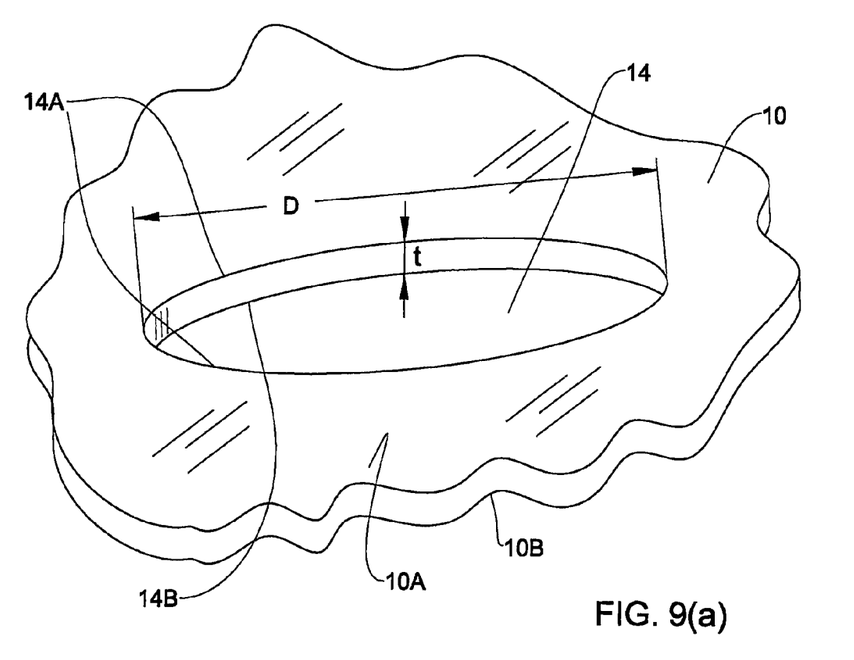
FIG. 9a is a view of a relatively thin object and background medium of the system of FIG. 1 as viewed along the optical axis of the image capturing device thereof.
Figure 9B:
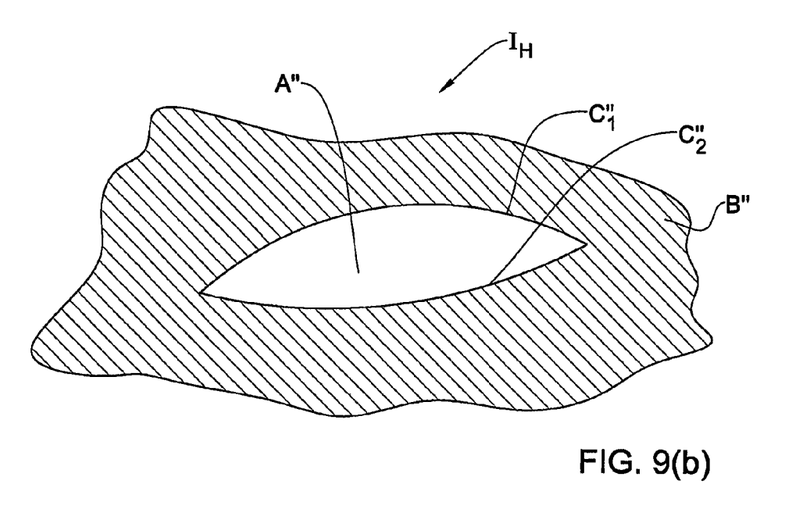

Referring to FIGS. 9(a) and 9(b), for example, in some applications, the object 10 may comprise a relatively small dimension in the thickness direction t, for example when the object constitutes a component fabricated from sheet metal. In such cases, some such bores may be shallow, wherein the thickness dimension t thereof may be small, though significant, relatively to the width or diameter D thereof. Accordingly, when the viewing axis OA is at angle θ to the axis of the bore (or hole) 14, the image $I_H$ taken thereof may be a composite of part the outer edge 14A of the hole 14 closest to the image capturing device, that is the edge of the hole on the surface 10A of the object facing the image capturing device, and part of the far edge or inner edge 14B of the hole, that is, of the edge of the hole on the other side 10B of the object away from the image capturing device. Thus image $I_H$ comprises a relatively dark region A", corresponding to the surface 10A, and a relatively bright region B" corresponding to the part of the background medium as seen via the hole 14. The demarcation between the two regions comprises two intersecting arcs—$C_1$" and $C_2$", wherein $C_1$" corresponds to the aforementioned part of outer edge 14A and $C_2$" corresponds to said part of inner edge 14B. In such a case, the two arcs can be analysed separately, and ellipses fitted to each arc separately such that the curvature of the best fit ellipse is the closest possible to the corresponding arc. Accordingly, dimensional data such as the diameter of the hole 14, at each face 14A, 14B of the object, can be determined, as well as the centers thereof and so on. The above example has been based on a substantially cylindrical hole 14, wherein the size and shape of the hole edges are the same on both faces 14A and 14B, and these are moreover aligned along an axis orthogonal to the faces. However, the method is similarly applicable, mutatis mutandis, to other types of holes, for example having a conical or stepped profile, in which the size and shape of the hole edges are not the same on both faces 14A and 14B, and/or that these may not necessarily be aligned along an axis orthogonal to the faces.

When the present invention is used for checking dimensional data, rather than for determining otherwise unknown dimensional data, of an object, such methods for applying best fit ellipses and so on to features in the image are typically more straightforward.

Similar analyses may be conducted on any geometrical feature of the object being scanned or imaged, mutatis mutandis.

Figure 4:
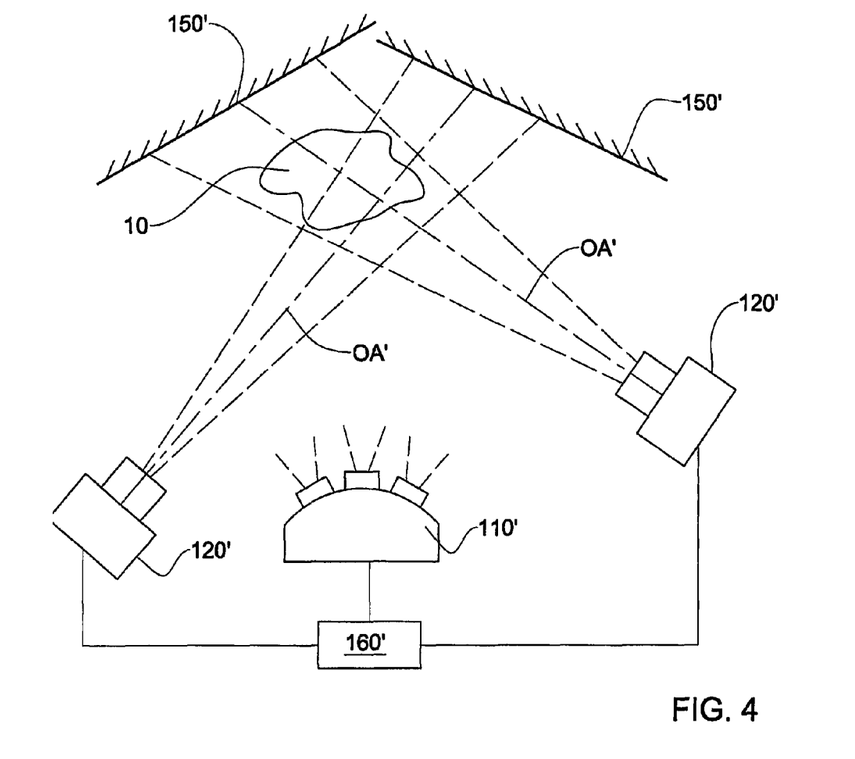
FIG. 4 is a schematic illustration of the elements of a variation of the first embodiment of the system of the invention.
Figure 5A:
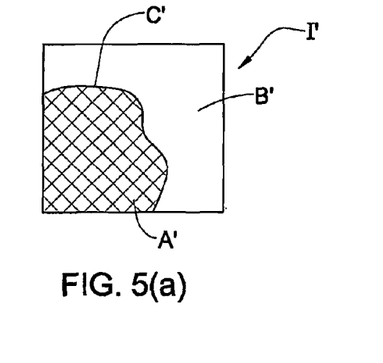
FIGS. 5a and 5b are images of the object and background media of the system of FIG. 4 taken by the two image capturing devices thereof.
Figure 5B:
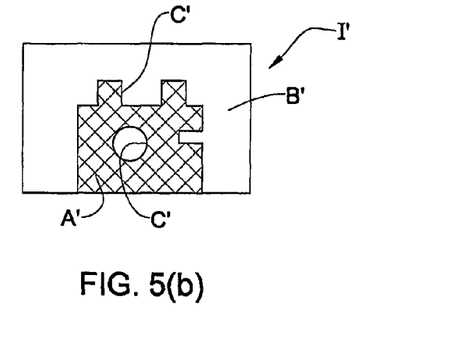

Thus, referring to FIGS. 4 and 5a, 5b, a variation of the first embodiment of the system, generally designated with the numeral 100', is configured to enable two predetermined edge profiles of an object 10 to be obtained. In this embodiment, the object 10 is placed in front of two light reflecting background media 150', and two optical image capturing devices 120' are provided, each one aligned with the object 10 and one or another of the media 150'. An illumination source 110' is provided for illuminating the object 10 as well as parts of the two light reflecting media 150' as seen by the two optical image capturing devices 120'. The object 10 is spatially arranged with respect to the image capturing devices 120' and the media 150' so that a predetermined edge of the object is seen by each one of the image capturing devices 120'. When illuminated by the source 110', image capturing devices 120' each capture an image I' of the corresponding edges as seen along the corresponding optical axes OA', each image comprising a dark area A' corresponding to the object, and a bright area B' adjacent corresponding to a part of the medium, and the interface or edge therebetween C' whose respective profiles may be analysed and compared with nominal profiles by means of processor 160'.

Clearly, more than two image capturing devices may be provided, with corresponding media aligned therewith and placed behind the object, such that a plurality of different parts of the object may be analysed according to the invention, similarly to the two devices described above, mutatis mutandis.

Thus, in this embodiment, it is not necessarily required to determine the three-dimensional profile of the edges, but rather to compare the 2D edges, as viewed from any particular orientation, with nominal edges, previously determined.

Figure 6:
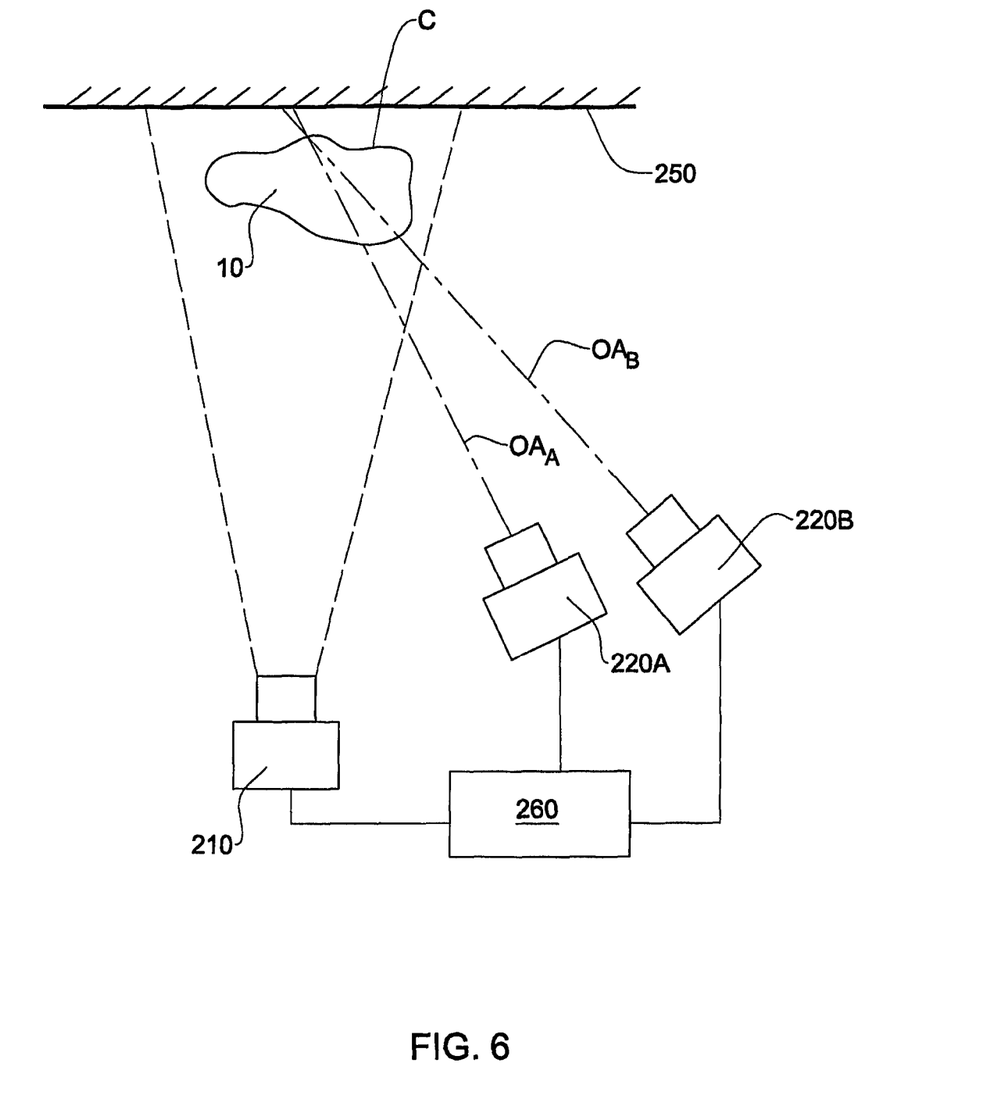
FIG. 6 is a schematic illustration of the elements of the second embodiment of the system of the invention.

In a second embodiment of the invention, the three-dimensional topography of the edges, optionally including the surface of the object at least close to the edges, may be determined. Referring to FIG. 6, the system according to the second embodiment, generally designated with the numeral 200, comprises at least two image capturing devices 220A, 220B which are configured to obtain images of the same edge C of object 10 together with a part of the reflecting medium 250 placed behind the object with respect to devices 220A, 220B.

The image capturing devices 220A, 220B are configured for transmitting images electronically to a microprocessor means 260 such as a suitable computer via an image grabber, for example. The microprocessor means 260 may also be configured to control the illumination source 210, typically to synchronize illumination of the object with the image taking process by means of the devices. 220A, 220B.

Figure 7A:
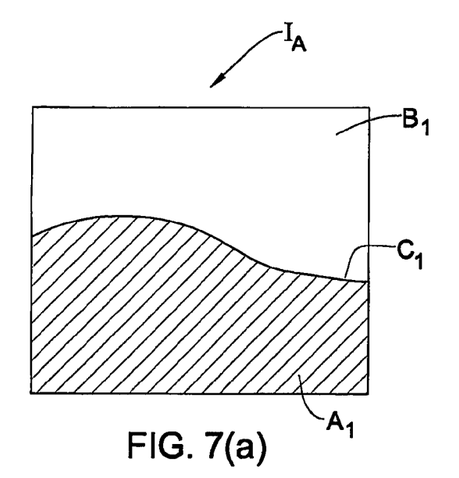
FIGS. 7a and 7b are images of the object and background medium of the system of FIG. 6 taken by the two image capturing devices thereof.
Figure 7B:
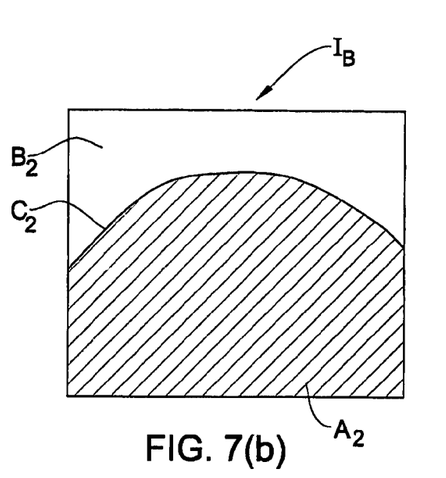

Illumination source 210, which may be similar, for example, to the illumination source described for the first embodiment, mutatis mutandis, illuminates the object such as to produce a sharp contrast between the object 10 and the background medium 250 when viewed by the devices 220A, 220B along the optical axes $OA_A$, $OA_B$, respectively. Each device 220A, 220B captures an image of the object 10, in particular comprising the same edge C, and FIGS. 7a and 7b illustrate typical images $I_A$, $I_B$ of object 10 so captured. As with the earlier embodiments, mutatis mutandis, image $I_A$ shows a relatively dark area A1 corresponding to the object, and a relatively bright area B1 corresponding to the medium 250, with the transition between the two areas, edge C1, corresponding to the mechanical edge C as viewed along $OA_A$. Similarly, image $I_B$ shows a relatively dark area A2 corresponding to the object, and a relatively bright area B2 corresponding to the medium 250, with the transition between the two areas, edge C2, corresponding to the mechanical edge C as viewed along $OA_B$.

Next, medium 250 is replaced with a regular non-highly reflective medium (not shown), and the object is illuminated in a manner such as to enable the 3D topography thereof to be determined. For example, the object is illuminated with a set of parallel lines or stripes, in a manner known in the art to enable 3D topographical data to be derived from a set of images of the stripes as illuminated on the object. Alternatively the medium 250 is not replaced with a less reflective medium, but rather is retained, and the object illuminated so as to determine the 3D topography thereof. In such a case it is possible for the typically highly reflective background provided by the medium 250 to interfere with the 3D reconstruction of the surfaces close to the edges, but will not generally interfere with other areas of the object that are distanced from the edges. Suitable image processing techniques, know per se in the art, may be used to resolve the influence of the reflection interference on the reconstruction near the edges.

There are many ways for illuminating the object with the stripes or any other suitable pattern. For example, a light emitter may be used having a mask, the mask enabling the stripe pattern to be illuminated onto the object. The mask can be a so-called "passive" mask, for example a mask defining a fixed stripe pattern, selectively locatable in the optical path of light generated by the light emitter, such as to enable regular light (i.e. without a stripe pattern) to be projected onto the object. Such a passive mask may be in the form of a rotating disc, one half of which comprises the stripe pattern, and the other half pattern being blank, and the disc is rotated by 180° to bring the required half in alignment with the light emitter.

Alternatively, the mask may be a so-called "active" mask, in the form of a spatial light modulator (SLM) operatively connected to a control module, and under the control of the latter, the SLM provides the required stripe pattern or uniform light.

Alternatively, the light emitter itself may be configured to generate structured light in the form of stripes. This may be implemented by using a matrix of light-emitting elements. Such a matrix may be designed in accordance with a fixed stripe pattern or uniform illumination, or may be configured as a suitable light emitting modulator, operatively connected to a control module, to selectively illuminate the object with the stripe pattern or uniform illumination.

When illuminated by said stripe pattern, images $I_A'$, $I_B'$ of these stripes $S_A$, $S_B$, respectively, are captured by the devices 220A, 220B, respectively. For this purpose, the devices 220A, 220B remain substantially at the same relative positions with respect to the object as before when images $I_A$, $I_B$ were taken.

On images $I_A$, $I_B$, the two-dimensional profile of the edge, C1 and C2, respectively, previously obtained, are superimposed, at least in a numerical or virtual sense by means of microprocessor means 260. Since the devices 220A, 220B, have not moved in their relative positions with respect to the object with respect to when the images $I_A$, $I_B$ were taken, the edge profiles Cl, C2 can be superimposed directly over the images $I_A$, $I_B$.

Movement of the object 10 relative to the image capturing devices 220A, 220B, should it occur can be dealt with in any suitable manner, for example as disclosed in WO 02/19687 entitled "Accurately Aligning Images in Digital Imaging Systems by Matching Points in the Images", co-assigned to the present Assignee, and the contents of which are incorporated herein by reference.

Figure 8A:
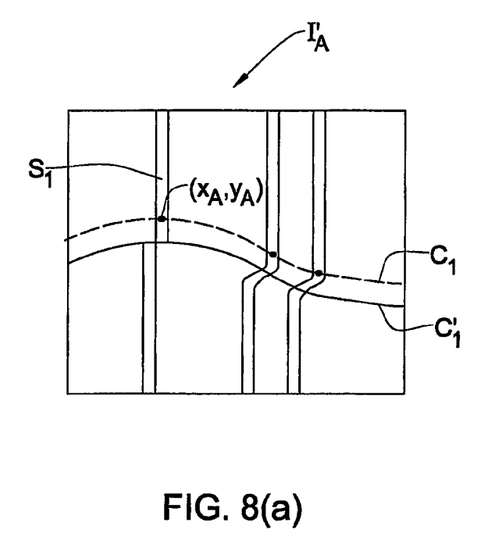
FIGS. 8a and 8b are images obtained when a particular 1-dimensional stripe pattern is illuminated onto the object of the system of FIG. 6, and taken by the two image capturing devices thereof.
Figure 8B:
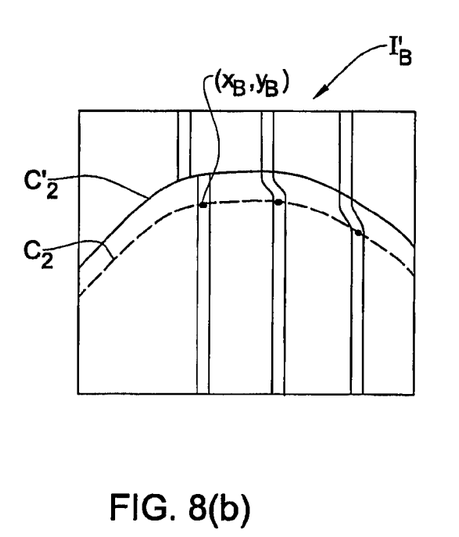

As indicated by the dotted lines C1, C2 in FIGS. 8a and 8b, respectively, the position of the true mechanical wedges of the object 10, as seen from the direction of devices 220A, 220B, is indicated by C1, C2 respectively. On the other hand, the original images $I_A$, $I_B$ may also comprise an approximation to these edges, marked as C1' and C2' respectively, which may appear to be displaced or appear distorted with respect to C1 and C2, respectively, due to the edge effects discussed in the background section above.

In the next step, the intersection coordinates between each stripe, as viewed in image $I_A'$, and the profile C1 is determined. For example for stripes $S_A$ in image $I_A'$, the intersection points are at $(x_A, y_A)$. Similarly, the intersection points at $(x_B, y_B)$ between profile C2 and the stripes $S_B$ in image $I_B'$ are found.

In the next step, any suitable method may be employed for labeling at least the portion of the stripes SA comprising the corresponding intersection points $(x_B, y_B)$ in image $I_a'$, with the corresponding portion of stripes $S_B$ in image $I_B'$, such that proper identification of the intersection points between the images can be determined. This is necessary in order to overcome the problem of ambiguity that may occur, particularly when the object is itself complex and comprises steep edges or steep surfaces, as is often the case for manufactured items.

For example, the method disclosed in WO 2005/010825, the contents of which are incorporated herein in their entirety by reference, assigned to the present Assignee, may be used for such labeling. The disclosed method is based on enabling unique matching of each reflected point on an object with an illuminating pattern using a two stage approach, such matching being possible at the sub-pixel level. In the first stage, which generally but not necessarily is carried out before the striped image set of FIGS. 8a and 8b are obtained, a first set of images of the object is obtained, and a spatial coding technique is used for correspondence mapping of coordinates from a first image to a second image (of the first set) of an object. Neighborhood coding techniques are typically used for determining this correspondence. Optionally, a random grid or other structured light is used to illuminate the object, and the images are obtained at different angles with respect to the object. Alternatively, surface features of the object may be sufficient to enable the aforesaid mapping to be effected from images obtained using unstructured light. In the second stage, a second structured illumination, typically comprising a striped grid, for example the stripe pattern used in the embodiment of FIG. 6, is used to obtain a second set of images, typically comprising two further images of the object such as illustrated in FIGS. 8a and 8b, and the mapping provided by the first stage provides proper labeling of the grid between these two images of the second set. The first set of images typically comprises two images at different angles with respect to said object.

Thus, a matching at least of elements corresponding to intersection points between the images $I_A'$, $I_B'$ is obtained according to the following method steps:

(a) obtaining a first set of images (not illustrated) of the object having a first structured pattern on the surface thereof, and determining correspondence of image points between images of said first set of images;

(b) obtaining a second set of images, $I_A'$, $I_B'$, of the object having a second structured pattern thereon, and labeling said second structured pattern, $S_A$, $S_B$ between images of said second set of images based on the correspondence determined in (a);

(c) matching elements corresponding to the intersection points $(x_A, y_A)$ of one image $I_A'$ with the elements corresponding to the intersection points $(x_B, y_B)$ of the other image $I_B'$ of said second set of images based on the labeling determined in (b).

Once the element of a stripe in image $I_B'$ having the intersection point $(x_B, y_B)$ corresponding to the intersection point of an element $(x_A, y_A)$ of image $I_A'$ is found, any suitable method may be implemented to determined the 3D coordinates of the corresponding intersection point, for example based on triangulation or epipole methods or any other suitable method, for example as disclosed in the aforesaid WO 2005/010825.

In this manner, the 3D spatial coordinates, and thus the full 3D profile of the edge C may be determined.

In a preliminary step, the image capturing devices 220A, 220B must be calibrated, for example as disclosed in U.S. Pat. No. 6,125,197 or in "Image-variant Interior Orientation and Sensor Modelling of High-Quality Digital Cameras" by H. Hastedt et al. ISPRS Symposium Comm. V, Korfu, 2002, the contents of both articles being incorporated herein by reference.

Further, similar methods as known in the art, particularly as disclosed in the aforesaid WO 2005/010825, may be used for obtaining the 3D coordinates of the surface of the object away from the edge C being reconstructed.

The second embodiment of the invention generally provides more accurate results when the edge being investigated is fully visible from the viewing axis of all the image capturing devices.

In this embodiment of the invention, the two images in each set of images are captured as images, substantially simultaneously, either by using two cameras or any other suitable image capturing devices 220A, 220B. In other variations of this embodiment, a single camera or other suitable image capturing device may be used, and moved between two positions relative to the object, the positions being similar to those occupied by devices 220A, 220B in FIG. 6, for example. In such variations, the precise position of the single image capturing device is preferably accurately reproduced for each set of images taken. Alternatively, there are some methods, for example the bundle adjustment method used in photogrammetry, in which the 3D location of the fiducial or datum points and camera positions and locations are calculated from the multiple images taken from different angles. If there are sufficient fiducial points on the object that are detected in the images there may be no need for mechanically reproducing the exact location of the camera, but rather the camera location can be calculated from the image data. Accordingly, the different images taken at different camera locations can be adjusted to compensate for the different locations.

In other embodiments, more than two cameras may be used, each of which captures an image of the object in a similar manner to that described above, mutatis mutandis.

In the method claims that follow, alphabetic characters and Roman numerals used to designate claim steps are provided for convenience only and do not imply any particular order of performing the steps.

Finally, it should be noted that the word "comprising" as used throughout the appended claims is to be interpreted to mean "including but not limited to".

While there has been shown and disclosed exemplary embodiments in accordance with the invention, it will be appreciated that many changes may be made therein without departing from the spirit of the invention.

What is claimed is:

1. A method of determining edge data in procedures associated with the dimensional measurement of an object, comprising:
   (a) obtaining at least one image of a desired edge of a surface of an object contrasted with a background medium, wherein the surface including said edge and the background medium are front-illuminated, and wherein the background medium comprises a reflectance substantially greater than a reflectance of said surface at least in a vicinity of said edge, at least when viewed along an image viewing axis associated with said at least one image;
   (b) analysing said image to obtain edge data from an interface between adjacent areas of different optical contrast therein corresponding to one or the other of said surface and said background medium;
   wherein in step (a), said at least one image comprises at least one first image area corresponding to said portion of said surface comprising said at least one edge and at least one second image area corresponding to a portion of said background medium proximate to said at least one edge, wherein an interface between said first image area and said second image area corresponds to said at least one edge; and step (b) comprises determining the coordinates on said image corresponding to the interface,
   wherein said procedures include a procedure for determining the three dimensional profile of said edge.

2. A method according to claim 1, wherein step (a) comprises:
   aligning said surface and said edge with respect to a viewing axis of at least one image capturing device, such that said surface and edge are positioned intermediate between said at least one image capturing device and said background medium;
   front illuminating at least a portion of said surface including said edge and at least a portion of said background medium proximate to said edge;
   obtaining at least one image of at least said portion of said surface comprising said edge and including said portion of said background medium as viewed from said image viewing axis of said at least one image capturing device.

3. A method according to claim 1, wherein said background medium has a gain greater than unity.

4. A method according to claim 1, wherein said background medium comprises a retro-reflective layer.

5. A method according to claim 1, wherein said background medium has a gain greater than 2.

6. A method according to claim 1, wherein said procedures include a procedure for comparing a profile of said edge as viewed along a particular viewing axis with a datum profile.

7. A method according to claim 6, further comprising the step of determining geometrical parameters of said edge from said comparison.

8. A method according to claim 7, wherein said geometrical parameters include any one of: a center of curvature of the edge; a characteristic dimension of the edge; departure of the edge from a nominal profile.

9. A method according to claim 8, wherein said characteristic dimension includes any one of: a radius of curvature; diameter; width.

10. A method according to claim 1, wherein said object is a mechanical component.

11. A method according to claim 10, wherein said object is an automotive component.

12. A method according to claim 1, wherein said edge is an external edge of said object.

13. A method according to claim 1, wherein said edge is an internal edge of said object.

14. A method of providing edge data useful in procedures associated with the dimensional measurement of an object, comprising:
   (a) obtaining at least one image of a desired edge of a surface of an object contrasted with a background medium, wherein the surface including said edge and the background medium are front-illuminated, and wherein the background medium comprises a reflectance substantially greater than a reflectance of said surface at least in a vicinity of said edge, at least when viewed along an image viewing axis associated with said at least one image; and
   (b) analysing said image to obtain edge data from an interface between adjacent areas of different optical contrast therein corresponding to one or the other of said surface and said background medium,
   wherein said procedures include a procedure for determining the three dimensional profile of said edge, and
   wherein step (a) comprises obtaining a set of first images comprising at least two first images of said edge along different viewing axes, and the method further comprising the step of matching corresponding points of the edge between the at least two first images to obtain a series of matched points, and the step of determining the 3D profile of said edge from said series of matched points.

15. A method according to claim 14, wherein said 3D coordinates are determined using a suitable triangulation or epipole method applied to said matched elements.

16. A method of determining edge data in procedures associated with the dimensional measurement of an object, comprising:
（a) obtaining at least one image of a desired edge of a surface of an object contrasted with a background medium, wherein the surface and the background medium are front-illuminated, and wherein the background medium comprises a reflectance substantially greater than a reflectance of said surface at least in a vicinity of said edge, at least when viewed along an image viewing axis associated with said at least on image; and
(b) analyzing said image to obtain edge data from an interface between adjacent areas of different optical contrast therein corresponding to one or the other of said surface and said background medium,
wherein said procedures include a procedure for determining the three dimensional profile of said edge,
wherein step (a) comprises obtaining a set of first images comprising at least two first images of said edge along different viewing axes, and the method further comprising the step of matching corresponding points of the edge between the at least two first images to obtain a series of matched points, and the step of determining the 3D profile of said edge from said series of matched points, and
wherein said step of matching corresponding points between images comprises: illuminating said surface with a structured pattern and obtaining a set of second images of the thus illuminated object along said different viewing axes corresponding to said set of first images; for each said second image superimposing a corresponding first image, at least in a virtual sense, finding intersections between said pattern therein and a said interface of the corresponding said first image to provide a series of intersection points for said second image; matching elements corresponding to intersection points of one second image with the intersection points of another said second image; determining 3D coordinates from said matched elements.

17. A system for determining edge data in procedures associated with the optical measurement of surfaces of an object having at least one edge, comprising:
at least one image capturing device for capturing at least one image of at least said edge with respect to a viewing axis;
at least one background medium, wherein said background medium comprises a reflectance substantially greater than a reflectance of said surface of the object at least in a vicinity of said edge when viewed along at least along said viewing axis;
the at least one image capturing device being disposed with respect to said background medium such that said surface and edge are positioned intermediate between said at least one image capturing device and said background medium;
illumination means for front illuminating at least a portion of said surface including said edge and at least a portion of said background medium proximate to said edge;
microprocessor means for analysing image captured by said at least one image capturing device to obtain edge data from an interface between adjacent areas of different optical contrast therein corresponding to one or the other of said surface and said background medium wherein said at least one image comprises at least one first image area corresponding to said portion of said surface comprising said at least one edge and at least one second image area corresponding to a portion of said background medium proximate to said at least one edge, wherein an interface between said first image area and said second image area corresponds to said at least one edge and determining the coordinates on said image corresponding to the interface,
wherein said procedures include a procedure for determining the three dimensional profile of said edge.

18. A system according to claim 17, wherein the at least one image capturing device comprises two or more of said image capturing devices, and wherein each of said image capturing device is positioned at a different relative viewing axis with respect to said object.

19. A system according to claim 18, wherein said system comprises two or more of said background mediums, wherein each of said background medium is positioned such that the object is aligned between said background medium and at least one of said image capturing devices.

20. A system according to claim 17, wherein said background medium comprises a retro-reflective layer.

21. A system according to claim 17, wherein said background medium comprises a gain of greater than unity.

22. A system according to claim 17, wherein said background medium comprises a gain of about 2 or greater than 2.

* * * * *

UNITED STATES PATENT AND TRADEMARK OFFICE
CERTIFICATE OF CORRECTION

PATENT NO.         : 8,482,743 B2
APPLICATION NO.    : 11/665978
DATED              : July 9, 2013
INVENTOR(S)        : Avner Segev It is certified that error appears in the above-identified patent and that said Letters Patent is hereby corrected as shown below:

In the Claims

Column 14, Claim 1, Line 4

Please delete "procedure for determing"

and replace with -- procedure for determining --

Column 16, Claim 22, Line 50

Please delete "gain of about 2 or greater"

and replace with -- gain greater --

Signed and Sealed this
Twenty-fourth Day of December, 2013

Margaret A. Focarino
*Commissioner for Patents of the United States Patent and Trademark Office*